United States Patent [19]
Igel et al.

[11] Patent Number: 6,017,775
[45] Date of Patent: Jan. 25, 2000

[54] PROCESS FOR MANUFACTURING A SENSOR WITH A METAL ELECTRODE IN A METAL OXIDE SEMICONDUCTOR (MOS) STRUCTURE

[75] Inventors: Guenter Igel, Teningen; Hans-Jurgen Gahle, Emmendingen, both of Germany

[73] Assignee: Micronas Intermetall GmbH, Freiburg, Germany

[21] Appl. No.: 08/948,127

[22] Filed: Oct. 9, 1997

[51] Int. Cl.[7] .................................................. H01L 21/44
[52] U.S. Cl. ................................ 438/48; 438/98; 438/142
[58] Field of Search .................................. 438/48, 49, 97, 438/98, 50, 96, 488, 637, 650, 686, 700, 723, 724, 756, 757; 257/368, 414; 216/2

[56] References Cited

U.S. PATENT DOCUMENTS

| 4,948,257 | 8/1990 | Jain et al. ........................... 438/750 |
| 5,342,806 | 8/1994 | Asahina ............................. 638/650 |

*Primary Examiner*—Savitri Mulpuri
*Attorney, Agent, or Firm*—Arthur L. Plevy

[57] ABSTRACT

The invention relates to a process for manufacturing a sensor with a metal electrode in an MOS structure. During the MOS process, a sensing region with a structure for the metal electrode is formed, this structure being made of a material having predetermined adhesion properties for metals, the sensing region being uncovered by etching the passivating layer, and a metallization of the surface of the MOS structure being carried out in which the metal layer adheres only to the structure for the metal electrode.

20 Claims, 2 Drawing Sheets

PROCESS FOR MANUFACTURING A SENSOR WITH A METAL ELECTRODE IN A METAL OXIDE SEMICONDUCTOR (MOS) STRUCTURE

FIELD OF INVENTION

This invention relates to a process for manufacturing a sensor with a metal electrode in an MOS structure.

BACKGROUND OF INVENTION

Processes for manufacturing metal oxide semiconductor (MOS) devices, such as field effect transistors (MOSFETS) are well known. However, manufacturing problems arise when attempting to form sensors having metal electrodes using a MOS structure. The manufacture of such sensors has failed in practice because conventional processes for forming a metal electrode cannot be combined with the conventional MOS process. With the conventional MOS process, additional process steps are necessary to deposit the metal electrode, particularly photolithographic, etching, and resist-stripping steps. If the metal electrodes are formed from the materials commonly used for them, namely noble metals, such as gold or platinum, the MOS structure is contaminated by the metal when the above process steps are carried out. This adversely affects the properties of silicon oxide, and particularly the properties of the gate oxide and the underlying channel in the case of MOS transistors. Furthermore, the apparatus used in the semiconductor factory to carry out the process steps will also be contaminated, which is not permissible in MOS fabrication. If a metal electrode of a base metal, such as aluminum or titanium, is deposited, these metals will change their properties during deposition and on contact with other materials. As a result, the properties of the sensor will change as well. If platinum is used for the metal electrode, a bonding agent is required, for which titanium is often employed. In that case, the above-described unfavorable properties will combine. In addition, the process, because of the additional steps required to deposit the metal electrode, become increasingly complex and expensive.

Accordingly, a more economical method for providing a sensor with a metal electrode in an MOS structure which delivers reliable sensor signals is greatly desired.

SUMMARY OF THE INVENTION

A process for manufacturing a sensor with a metal electrode in an MOS structure wherein the MOS structure is fabricated with a conventional MOS process up to the formation of a passivating layer, a sensing region with a structure for the metal electrode being formed during the MOS process, the structure for the metal electrode being made of a material having predetermined adhesion properties for metals, the sensing region being uncovered by etching the passivating layer and any layers located between the sensing region and the passivating layer, and a metallization of the surface of the MOS structure being carried out in which the metal layer adheres only to the structure for the metal electrode.

In a first embodiment of the invention, the metallizing is done by plating, particularly by electroless plating. In that case, the material of the structure for the metal electrode and the metal to be deposited must be suitably chosen.

In a second embodiment, the metal is deposited by evaporation over the entire surface of the MOS structure provided with the patterned passivating layer. The metal layer thus produced must then be selectively removed. This is done by subjecting the MOS structure to an ultrasonic treatment

BRIEF DESCRIPTION OF DRAWINGS

The invention will now be explained in more detail with reference to the accompanying drawings.

DETAILED DESCRIPTION OF INVENTION

Figure 1:
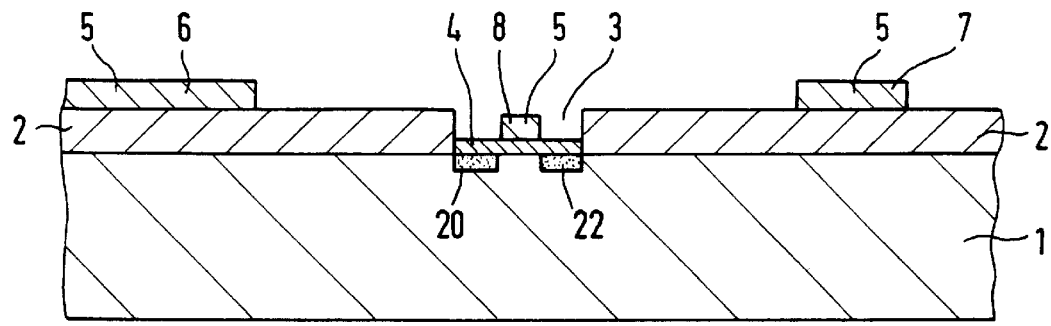
FIGS. 1 to 3 show cross sections of an embodiment of an MOS structure fabricated with the process according to the invention, after different process steps.

FIG. 1 shows a semiconductor substrate 1 on which a field oxide layer 2 was deposited. Semiconductor substrate 1 may be of silicon or polysilicon, for example, and field oxide layer 2 may be of silicon dioxide. Field oxide layer 2 has an opening 3 in the place where an MOS transistor is to be provided. FIG. 1 shows the source region 20, drain region 22 and a gate region comprising the gate electrode 8 and gate oxide layer 4. In opening 3, a gate oxide layer 4 was deposited which is substantially thinner than field oxide layer 2. A polysilicon layer 5 deposited on field oxide layer 2 and gate oxide layer 4 is patterned in such a way as to form a gate electrode 8 on gate oxide layer 4, and a bonding region interconnection 6 and a sensing region 7 on portions of field oxide layer 2. Sensing region 7 has structure for the metal electrode to be formed thereon. In the embodiment shown, the sensing region serves to support a flat metal electrode. It is advantageous that the sensing region is made of silicon or polysilicon, with the area outside the structure for the metal electrode being covered with a material which adheres to metal less well than polysilicon. If one starts with a silicon wafer, silicon layers suitable for forming a sensing region are already present as a result of the process for fabricating an MOS structure containing at least one MOS transistor. The polysilicon of sensing region 7 may also have a spatially different structure, such as a comb structure for forming an interdigitated capacitor. To accomplish this, the polysilicon of sensing region 7 may be patterned in such a way as to uncover field oxide layer 2 in the places not to be covered with the metal electrode. Note that the sensing region may be formed either on the substrate itself or on a silicon layer produced during the MOS process. For example, it may be formed simultaneously with the deposition of polysilicon on the gate regions of the MOS transistors for forming gate electrodes. Furthermore, it is advantageous to cover the area outside the structure for the gate electrode 8 with an oxide, such as silicon oxide, since the process steps necessary for this are typically carried out during the fabrication of an MOS structure in a silicon semiconductor.

The process steps involved in producing the structure described so far correspond to conventional MOS process steps. The details necessary to carry out these steps are familiar to those skilled in the art. It must be ensured that sensing region 7 is defined during the fabrication of the structure, particularly of the MOS transistor. In the embodiment shown, sensing region 7 is formed simultaneously with silicon gate electrode 8 and interconnection 6.

Figure 2:
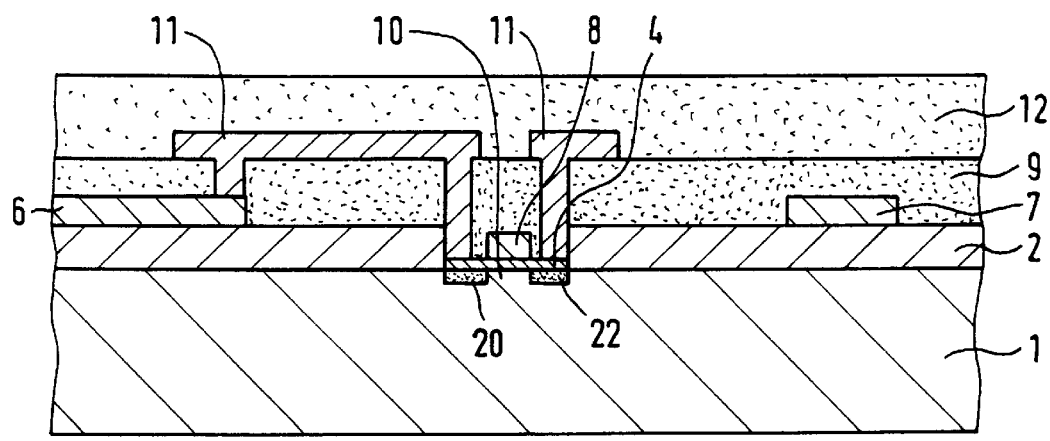

As shown in FIG. 2, an insulating layer 9 is subsequently deposited in which openings are formed above the desired contact areas, particularly above MOS transistor 10 and interconnection 6. In the preferred embodiment, the insulating layer 9 is a layer of silicon dioxide, which is disposed over the field oxide layer 2 and each of the sensing region 7, gate electrode 8 and bonding region interconnection 6. A conductor layer 11 is deposited on insulating layer 9 such that the openings in insulating layer 9 are filled with the material of conductive layer 11 to form the electric contacts with the gate oxide layer 4 of the MOS transistor 10, thereby permitting electrical communication between the bonding region interconnection and the MOS transistor 10. The entire MOS structure is then covered with a protective layer 12 to form a planar passivating layer. Conductor layer 11 is, as a rule, an aluminum layer.

Figure 3:
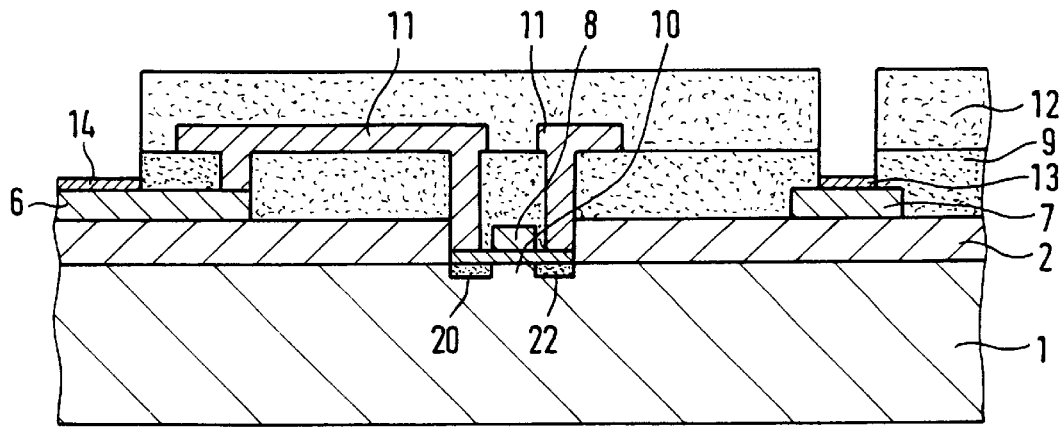

Openings are then etched into passivating layer 12 and insulating layer 9 to uncover portions of sensing region 7 in the area where a metal electrode 13 is to be deposited. At the same time, regions of interconnection 6 are uncovered for the formation of bonding pads. Then, the surface of the MOS structure is metallized such that the metal layer adheres only to the structure of the sensing region for the metal electrode and to the uncovered regions of the interconnection 6 for the bonding pads. In this manner, metal electrode 13 and bonding pad 14 are formed, as shown in FIG. 3.

The formation of metal electrode 13 and bonding pads 14 is made possible by the fact that the structure of sensing region 7 for metal electrode 13 and the regions for bonding pads 14 are formed of a material which adheres well to the metal, whereas passivating layer 12 and insulating layer 9 are formed of a material to which the material of the structure for metal electrode 13 and for bonding pads 14 adheres less well. Suitable materials are polysilicon for bonding region interconnection 6 and sensing region 7, palladium for metal electrode 13 and bonding pads 14, silicon dioxide for insulating layer 9, and silicon nitride and/or silicon oxide for passivating layer 12.

In one embodiment of the invention, the selective metallizing is done by plating, particularly by electroless plating. In that case, the metal to be deposited must be a more noble material than that of the base (i.e. sensing region 7 and bonding region interconnection 6), as is the case with the above-described choice of materials.

In an alternative embodiment of the invention, the metallizing is done by vapor deposition of a metal and subsequent selective, material-dependent removal of the metal layer using ultrasonic energy. If the material of the structure for the metal electrode and bonding pad, the material surrounding this structure, and the metal are suitably chosen, the deposited metal outside the structure can be reliably and easily removed by the ultrasonic treatment. No process steps which adversely affect the MOS structure or no costly process steps associated with a masking operation are necessary. Advantageously, a noble metal, particularly palladium, is used for the metallization. Selective adherence of the palladium to the sensor structure is ensured. It is also advantageous to treat the metal layer with a hydrogen-containing gas prior to its removal. The selective removal of the metal layer will then be more reliable and faster.

In the second embodiment described above, the metal is deposited by evaporation over the entire surface of the MOS structure provided with the patterned passivating layer 12. The metal layer thus produced must then be selectively removed. This is done by subjecting the MOS structure to an ultrasonic treatment during which the metal layer separates from passivating layer 12 and insulating layer 9. Prior to the ultrasonic treatment, the MOS structure may be treated with a hydrogen-containing gas. Since the metal layer, if made of palladium, takes up hydrogen, this results in easier separation of the metal layer from passivating layer 12. The adhesion properties of polysilicon and palladium are such that the palladium layer will not separate from the polysilicon even during an ultrasonic treatment. In the embodiment shown in FIG. 3, the structure of the sensing region includes an inner area to which a flat metal electrode will adhere. It is also possible to form other structures, particularly interdigitated capacitor structures, with this process.

As previously described, simplification of the process is achieved if during the etching of the passivating layer and any other layers for uncovering the sensing regions, regions for bonding pads are uncovered. No additional masking and etching steps are needed for this. The regions for the bonding pads may be of silicon and be formed in the same masking step as the sensing regions. In this manner, no aluminum, which is commonly used for forming conductive paths and for making contact, is brought out of the interior of the semiconductor. If the sensor is used as a biosensor or a chemical sensor, the entire MOS structure may be covered with a liquid to be examined, since the liquid cannot come into contact with the aluminum; aluminum and aluminum alloys dissolve in liquids and are poisonous to living organisms, such as cells. This embodiment involves no changes in the MOS fabrication process and in the properties of the MOS structure in principle.

Figure 4:
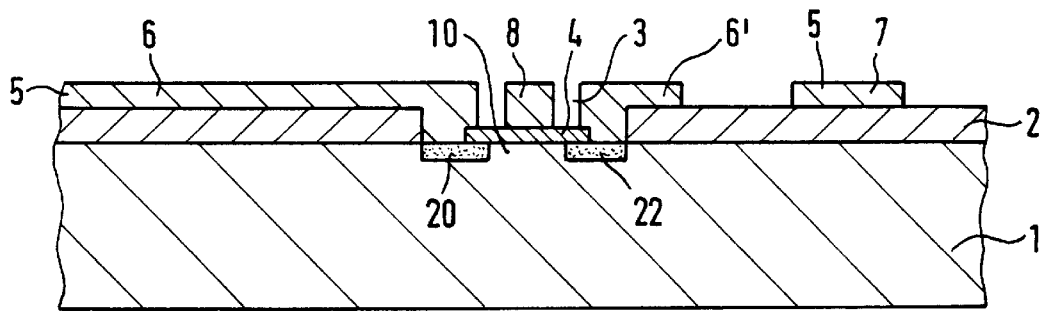
FIGS. 4 and 5 show a second embodiment of a sensor fabricated with the process according to the invention, after different process steps.
Figure 5:
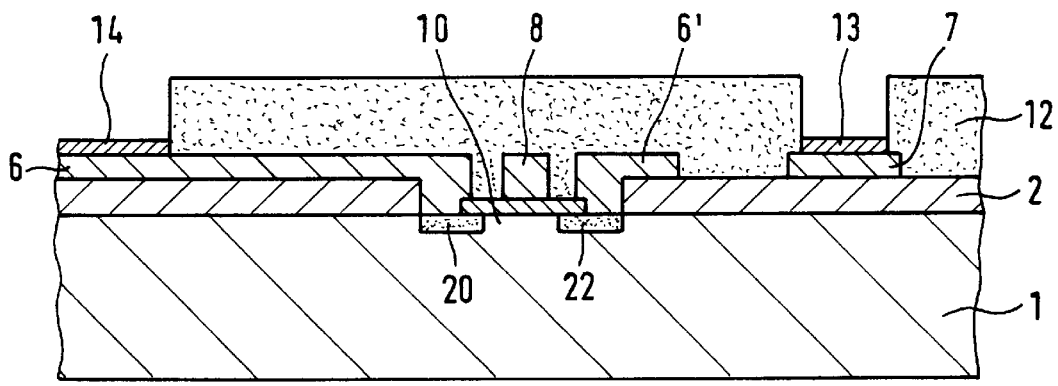

In another embodiment of the invention, shown in FIGS. 4 and 5, the electric interconnections of the MOS structure are formed of silicon. A thinner MOS structure can thus be fabricated, since the passivating layer can be made substantially thinner than in the case where the interconnections are of aluminum and a thicker passivating layer is needed. The structure also becomes thinner because the aluminum layer and additional insulating layers required for the latter are avoided. The avoidance of the use of aluminum makes it possible to carry out process steps at higher temperatures.

Referring now to FIGS. 4 and 5, there is illustrated the fabrication of another embodiment of an MOS structure with the process according to the invention. Unless otherwise described in the following, this structure is fabricated with the process described in connection with FIGS. 1 to 3, wherein like parts are indicated by like reference numerals. FIG. 4 shows the structure after field oxide layer 2 with opening 3 was deposited on semiconductor substrate 1. To form an MOS transistor in opening 3, a gate oxide layer 4 is deposited there, which, in this embodiment, is patterned in such a way that contact openings are provided between field oxide layer 2 and gate oxide layer 4 which expose the surface of the semiconductor substrate. In this manner, direct contact is made possible between MOS transistor 10 formed on substrate 1 and polysilicon layer 5 deposited on field oxide layer 2. In the embodiment shown, polysilicon layer 5 is patterned to form sensing region 7, gate electrode 8, and interconnections 6, 6'. Interconnections 6, 6' can be used both to make contact to MOS transistor 10 and to form bonding pad 14 (FIG. 5).

As shown in FIGS. 4 and 5, a layer of material, preferably polysilicon, is deposited onto a first portion of the field oxide layer 2 to form sensing region 7; depositing onto a second portion of the field oxide layer and extending to contact a first portion of the gate oxide layer 4 and substrate forms bonding region interconnection 6; depositing onto a second portion of the gate oxide layer 4 forms gate electrode 8; and depositing onto a third portion of the field oxide layer 2 and extending to contact a third portion of the gate oxide layer 4 and substrate forms interconnect region 6'. Cavities are thus formed between gate electrode 8 and bonding region interconnections 6 and 6', as well as between interconnection 6' and sensing region 7. Protective layer 12 is then formed over all of these regions to form a planar passivating layer of silicon nitride or silicon dioxide over the entire structure. The passivation layer 12 is then etched to uncover portions of the sensing region 7 for forming a metal electrode thereon, and bonding region interconnection 6 for forming bonding pads 14.

FIG. 5 shows this structure after passivating layer 12 with openings for the structure of sensing region 7 for metal electrode 13 and for bonding pad 14 were formed and after a metal layer was selectively deposited in the openings onto the uncovered silicon areas, i.e., onto the structure of sensing region 7 and onto the areas for bonding region interconnection 6, with one of the processes described above. Since this embodiment uses silicon interconnections, the deposition of additional aluminum interconnections (11 in FIG. 2) and intermediate insulating layers (9 in FIG. 2), shown in FIGS. 2–3, is avoided, so that the process becomes simpler and a thinner MOS structure can be achieved. Moreover, since the use of aluminum is avoided, the structure is resistant to treatments at high temperatures, so that high-temperature processes can be carried out during its fabrication. Compared to a conventional MOS structure with aluminum interconnections, the other electrical properties due to the higher electrical resistance of the interconnections must be taken into account.

From the foregoing discussion, one can ascertain that in the process according to the invention, the MOS structure fabricated with the conventional process steps up to the formation of the passivating layer, serves to protect the MOS structure. During this standard MOS process, a sensing region with a structure for the metal electrode is formed. For the sensing region and the structure for the metal electrode, materials can be chosen which are necessary for the MOS structure. No additional masks are needed for the formation of the sensing region and the structure for the metal eletrode. The sensing region and the structure for the metal electrode can be formed during the generation of masks which are used in the MOS process. After the fabrication of the MOS structure with the passivating layer, the latter is etched to uncover the sensing region. If any other layers are provided between the passivating layer and the sensing region, they will be etched correspondingly. This etching step can be carried out together with other etching steps and requires no additional mask, either. To form the metal electrode, the structure for it is metallized. This requires no additional mask, either, since a metallizing process is used in which the entire surface of the MOS structure is treated while the metal adheres only to the structure for the metal electrode. The material of the structure for the metal electrode and the metal are chosen to have suitable adhesion capabilities. Thus, the process according to the invention is very simple, since it eliminates the need for additional process steps in the formation of the metal electrode. In particular, however, only this makes it possible to combine the formation of a metal electrode with an MOS process. Since the formation of the metal electrode requires no photolithographic, etching, or resist-stripping steps, the metal electrode can be made of noble metals, without the MOS structure or the apparatus for carrying out the MOS process being contaminated.

What is claimed is:

1. A method of manufacturing a sensor with a metal electrode while fabricating a metal oxide semiconductor (MOS) structure, said method comprising the steps of:

forming a gate region, a source region, and a drain region of the MOS structure on a substrate;

forming a sensing region on top of said substrate from a material having predetermined adhesion properties for metals;

disposing a passivating layer on top of said substrate and said sensing region, said passivating layer having metal adhesive properties less than those of said sensing region;

etching said passivating layer to uncover a bonding region and said sensing region, said bonding region and said passivating layer defining a top surface of said structure wherein said bonding region is formed of the same material as said sensing region during the step of forming said sensing region; and, metallizing the top surface of said MOS structure to form a metal layer, wherein said metal layer adheres to said bonding region, and wherein said metal electrode is formed on said sensing region.

2. The method according to claim 1, wherein the step of metallizing said top surface comprises electroless plating.

3. The method according to claim 1, wherein the step of metallizing said top surface comprises the steps of:

vapor deposition of a metal onto said top surface; and selective removal of said metal layer using ultrasonic energy.

4. The method according to claim 1, wherein the step of metallization uses a noble metal, and wherein the sensing region comprises a less noble material than said noble metal.

5. The method according to claim 4, wherein said noble metal is palladium.

6. The method according to claim 3, further comprising the step of treating said metal layer with a hydrogen-containing gas prior to its selective removal.

7. The method according to claim 1, wherein said sensing region is made of polysilicon.

8. The method according to claim 7, wherein the step of disposing said passivating layer comprises disposing a silicon oxide layer.

9. The method according to claim 8, wherein the step of disposing said passivating layer further comprises disposing a silicon dioxide layer beneath said silicon oxide layer.

10. The method according to claim 1, further comprising the step of forming said a bonding region on said field oxide layer, and wherein the step of metallizing said top surface further includes metallizing said bonding region to form a bonding pad.

11. The method according to claim 10, further comprising the step of disposing a conductive layer of aluminum onto said gate oxide layer and extending to said bonding region to provide electrical communication therebetween.

12. A method of manufacturing a sensor with a metal electrode while fabricating a metal oxide semiconductor (MOS) transistor structure, said method comprising the steps of:

forming a gate region, a source region, and a drain region of the MOS transistor structure on a substrate, said gate region including a gate electrode disposed on a gate oxide layer;

forming a field oxide layer on said substrate, said field oxide layer having an opening for said gate, source and drain regions;

depositing a first layer of polysilicon onto a first portion of said field oxide layer to form a sensing region and a second layer of polysilicon onto a second portion of said field oxide layer to form a bonding region;

depositing an insulating layer onto said field oxide layer to cover said sensing region and a portion of said bonding region;

depositing a conductive layer of aluminum onto said insulating layer, said conductive layer in contact with said bonding region and said gate oxide layer to provide electrical communication therebetween;

depositing a protective layer on top of said insulating layer and said conductive layer to form a planar passivation layer on said MOS structure;

etching said protective layer and said insulating layer to uncover a portion of said sensor region and said bonding region, said uncovered sensor region, uncovered bonding region, and protective layer defining a top surface of said MOS structure;

metallizing said top surface of said MOS structure to form a metal layer, wherein said metal layer adheres only to said uncovered sensing region and bonding region, thereby forming a metal electrode and bonding pad respectively.

13. The method according to claim 12, wherein the step of metallizing said top surface comprises electroless plating.

14. The method according to claim 12, wherein the step of metallizing said top surface comprises the steps of:

vapor deposition of palladium metal onto said top surface; and selective removal of said metal layer using ultrasonic energy.

15. The method according to claim 12, wherein said insulating layer is silicon dioxide.

16. The method according to claim 12, wherein said protective layer is silicon oxide.

17. The method according to claim 14, further comprising the step of treating said metal layer with a hydrogen-containing gas prior to its selective removal.

18. A method of manufacturing a sensor with a metal electrode while fabricating a metal oxide semiconductor (MOS) transistor structure, said method comprising the steps of:

forming a gate region, a source region and a drain region of the MOS transistor structure on a substrate, said gate region including a gate oxide layer disposed over and in contact with said source and drain regions;

forming a field oxide layer on said substrate, said field oxide layer having an opening between said drain region and said source region;

depositing a first layer of polysilicon onto a first portion of said field oxide layer to form a sensing region;

depositing a second layer of polysilicon onto a second portion of said field oxide layer and extending to contact a first portion of said gate oxide layer to form a bonding region;

depositing a third layer of polysilicon onto a second portion of said gate oxide layer to form a gate electrode, wherein a first cavity is formed between said second and third polysilicon layers;

depositing a fourth layer of polysilicon onto a third portion of said field oxide layer and extending to contact a third portion of said gate oxide layer to form an interconnect region, wherein a second cavity is formed between said third and fourth polysilicon layers, and a third cavity is formed between said first and fourth polysilicon layers;

depositing a protective layer onto said field effect oxide layer to cover each of said polysilicon layers and corresponding cavities to form a planar passivation layer on said MOS structure;

etching said protective layer to uncover a portion of said sensor region and said bonding region, said uncovered sensor, uncovered bonding region, and protective layer defining a top surface of said MOS structure; and metallizing said top surface of said MOS structure with palladium to form a palladium metal layer, wherein said palladium metal layer adheres only to said uncovered sensing region and bonding region to form a metal electrode on said sensing region and a bonding pad on said bonding region.

19. The method according to claim 18, wherein the step of metallizing said top surface comprises electroless plating.

20. The method according to claim 18, wherein the step of metallizing said top surface comprises the steps of:

vapor deposition of said metal onto said top surface; and selective removal of said metal layer using ultrasonic energy.

* * * * *